US005158546A

United States Patent [19]

Haber et al.

[11] Patent Number: 5,158,546

[45] Date of Patent: Oct. 27, 1992

[54] CONTROLLED ACTION SELF-MIXING VIAL

[75] Inventors: Terry M. Haber, Lake Forest; Clark B. Foster, Laguna Niguel; William H. Smedley, Lake Elsinore, all of Calif.

[73] Assignee: Habley Medical Technology Corp., Laguna Hills, Calif.

[21] Appl. No.: 741,779

[22] Filed: Aug. 7, 1991

[51] Int. Cl.[5] .................... A61M 37/00

[52] U.S. Cl. .................... 604/87; 604/89; 604/416

[58] Field of Search .................... 604/191, 201, 203, 204, 604/239, 411–416, 82, 87, 88–92; 206/221, 222, 218; 220/501, 502, 529, 530, DIG. 34

[56] References Cited

U.S. PATENT DOCUMENTS

| | | | |
|---|---|---|---|
| 2,665,690 | 1/1954 | Lockhart | 604/416 |
| 2,761,447 | 9/1956 | Hersee | 604/89 |
| 3,314,563 | 4/1967 | Mounier | 604/416 |
| 3,696,919 | 10/1972 | Miles | 604/416 |
| 3,796,303 | 3/1974 | Allet-Coche | 604/416 |
| 4,648,532 | 3/1987 | Green | 604/87 |
| 4,779,722 | 10/1988 | Hall | 206/221 |

*Primary Examiner*—John D. Yasko

*Attorney, Agent, or Firm*—Townsend and Townsend

[57] ABSTRACT

A controlled action mixing vial (2) includes an elongate mixing container (14) having a movable piston (18) and fluid pressure rupturable seal (20). One pharmaceutical (58) is housed within the mixing container between the seal and the piston. A supplemental container (28) is coaxially translatably mounted to the mixing container and contains a second pharmaceutical (62) between the mixing and supplemental containers. Collapsing the mixing and supplemental containers causes the rupturable seal to open permitting the second pharmaceutical to be driven into the mixing container to drive the piston along the mixing container. The mixing and supplemental chambers are threadably coupled (10, 32) so the mixing is accomplished in a controlled, slow manner.

11 Claims, 4 Drawing Sheets

CONTROLLED ACTION SELF-MIXING VIAL

CROSS-REFERENCE TO RELATED APPLICATIONS

This application is related to the following U.S. patent applications: Ser. No. 07/741,776 for Precision Syringe-Filling Mechanism and Application No. 07/741,777 for Syringe Filling and Metering Device for Pharmaceutical Containers, both being filed on the same day of this application, and Application No. 07/615,610, filed Nov. 19, 1990 now U.S. Pat. No. 5,114,411 for Multi-Chamber Vial, the disclosures of which are incorporated by reference.

BACKGROUND OF THE INVENTION

Safe and effective drug therapy by injection depends not only upon accurate diagnosis, but also on efficient and reliable introduction of the medical substance into the subcutaneous cellular tissue without introducing contaminants or ambient air. The applicable drug or pharmaceutical must first be drawn from the resident container or vial into a syringe before injection The integrity and features of the vial, therefore, are influential over the overall safety of the injection.

Typically, great care must be taken when a needle cannula of a syringe is used in conjunction with a vial containing a pharmaceutical to be administered to the patient. As the pharmaceutical is drawn out of the container via the needle cannula, precautions must be taken to avoid air being drawn into the syringe. In rigid vials, air must be introduced into the container to fill the void created as the liquid pharmaceutical is withdrawn. This volume of air then becomes susceptible to being mixed with the pharmaceutical or being drawn in through the needle cannula and creating air pockets in the syringe barrel. Catastrophic consequences could result if these air pockets are subsequently injected into the patient along with the liquid pharmaceutical. Also, drawing ambient air into the vial can introduce airborne contaminants to the pharmaceutical.

Problems associated with injections are further complicated when the medication to be administered must be stored as two separate component parts, then mixed, prior to injection. Dual chamber vials have been developed to facilitate storage and mixing of these two-component medications. Common examples of multipart medications include medications which must be mixed from a component A, usually a preservative or catalyst, and a component B, which is usually a pharmaceutical. Component A or component B may be in powder or crystalline form instead of liquid form.

Recently, dual chamber vials have been developed which allow an A component and a B component to remain separated in independent chambers within a single package until mixing is desired. The vial allows mixing of the component parts in that same unitary package. In an example of such a device is the MIX-0-VIAL two compartment vial manufactured by the Upjohn Company of Kalamazoo, Michigan. This device is a single vial container having two chambers separated by a small stopper. The septum is formed by a plunger-stopper at one end which is used to pressurize the contents of one chamber so to displace a plug lodged in a small orifice separating the two chambers. As the plunger stopper is displaced (by giving it an axial push), the plug floats freely into one of the chambers and is used as an agitator to mix the two component parts together. The two components are free to flow between chambers through the connecting orifice and thereby mix together. Although this device is a significant advance in dual chamber vials, the device has a significant disadvantage. Even when the two components are properly mixed, when a needle cannula penetrates the septum and draws out the mixed medication, air becomes entrapped in the vial as air enters to replace the removed liquid as the medication is withdrawn. Time consuming precautions must be taken to carefully avoid entrapping air in the syringe and injecting the same into the patient.

Pharmaceutical components are sometimes sensitive to how violently they are mixed. For example, certain lyophilized crystals of human growth hormone, when mixed with a liquid carrier, must be mixed slowly. Mixing too quickly can cause damage to the pharmaceutical. The mechanical crushing, shearing and tearing, which can accompany rapid mixing, break up the molecules into subcomponents which do not retain the same medical qualities.

SUMMARY OF THE INVENTION

The present invention is directed to a controlled action self-mixing vial which can be used with a conventional syringe or a multiple-dose syringe to permit the controlled mixing of two pharmaceutical components or pharmaceuticals and the aspiration or delivery of the mixed pharmaceutical into the syringe without the introduction of air into the vial.

The controlled action mixing vial is used to mix two pharmaceutical components, at least one being liquid, in a controlled fashion for subsequent aspiration into a syringe. The vial includes an elongated mixing chamber having a piston which moves from a pre-mixed position towards the inner end of the mixing container to a post-mixed position towards an outer end of the mixing container. A fluid pressure rupturable seal is positioned at the inner end of the mixing container. One pharmaceutical component is stored within a first variable volume mixing region within the mixing container between the seal and the piston.

An axially translating supplemental container is mounted over the inner end of the mixing container. A second variable volume region is defined between the mixing and supplemental containers; a second pharmaceutical component is stored within the second variable volume container. Collapsing the mixing and supplemental containers causes the rupturable seal to open permitting the second component within the second variable volume region (which is a liquid) to be driven into the first variable volume region to mix with the first component (which can be a liquid or a solid) causing the piston to move axially towards the outer end of the mixing container. This collapsing of the mixing and supplemental containers is accomplished in a controlled, preferably slow manner by threadably coupling the two containers. That is, threads associated with the mixing and supplemental containers are used to axially drive the containers towards one another so that the mixing occurs is a controlled manner. Other driving structure, such as an axial ratchet drive, could be used instead of the threaded drive.

One of the primary advantages of the invention is that it permits users to easily and simply control how vigorously two pharmaceuticals are mixed.

Other features and advantages of the invention will appear from the following description in which the preferred embodiment has been set forth in detail in conjunction with the accompanying drawings.

DESCRIPTION OF THE PREFERRED EMBODIMENT

Figure 1:
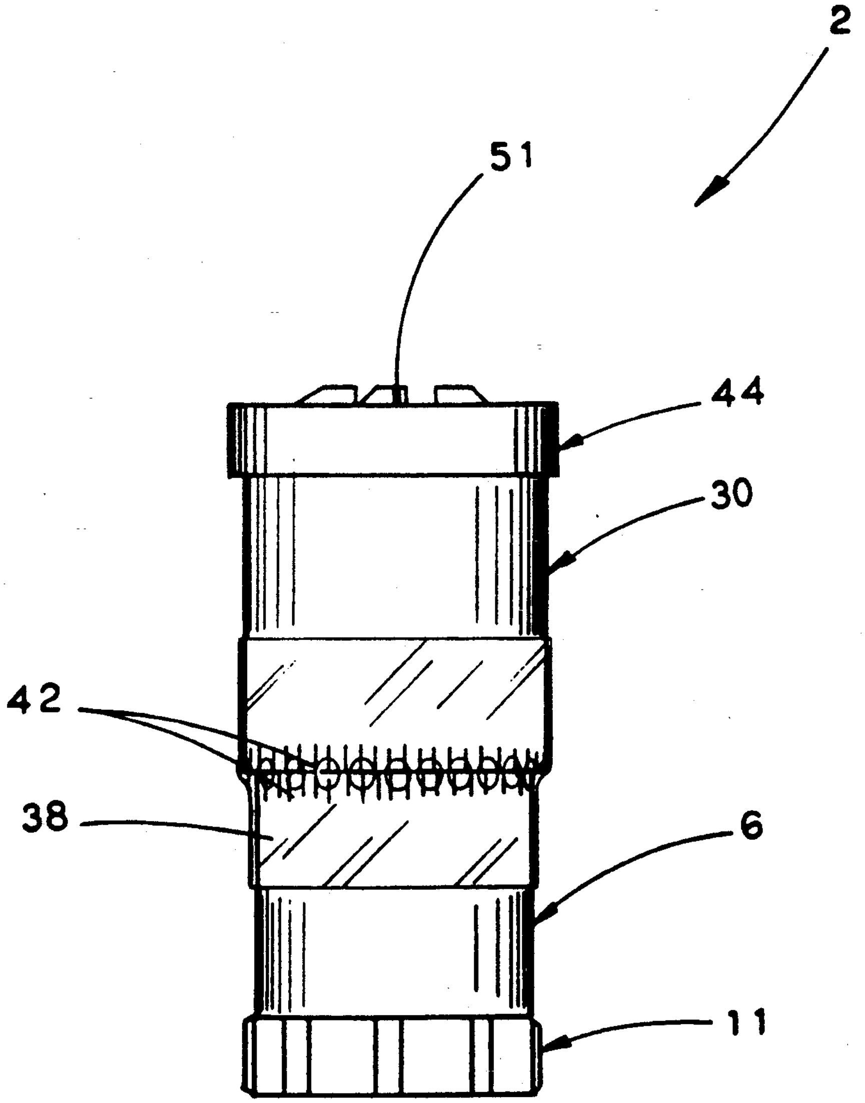
FIG. 1 is a side view of a controlled action mixing vial made according to the invention.

The figures illustrate a controlled action mixing vial 2 used with a generally conventional syringe 4. Mixing vial 2 includes a cylindrical cup housing 6, having a hole 8 at one end and external threads 10 at the other end. Cup housing 6 is made of a clear, shatter resistant plastic, such as radiation sterilizable acrylic or polycarbonate, and is sized to house a glass cup 12. The fit of glass cup 12 within cup housing 6 is quite snug so that hole 8 permits any air trapped within cup housing 6 to escape during assembly with glass cup 12. A cup 11 is secured to end 13 of cup housing 6 to provide the user with a good gripping surface for the purposes discussed below.

Mixing vial 2 also includes a mixing container 14 made of a glass cylinder 16 housing a pharmaceutically compatible elastomeric piston 18 and a barrier seal 20 at inner end of 22 of cylinder 16. Barrier seal 20 includes an elastomeric seal 24 and a plastic insert 26. See FIGS. 2A-2D. Barrier seal 20 and glass cup 12 combine to create a supplemental container 28.

Mixing container 14 is threadably coupled to supplemental container 28 using a threaded driver 30. Threaded driver 30 includes internal threads 32, which engage external threads 10 of cup housing 6, and an annular shoulder 34 against which an outer end 36 of cylinder 16 rests. A shrink-wrap tamper-evident seal 38 is applied at an end 40 of driver 30 to overlap onto cup housing 6. Both cup housing 6 and driver 30 have fine serrations 42 to provide for enhanced gripping of seal 38 against any relative rotary motion of housing 6 and driver 30. After removal of seal 38, threaded driver 30 can be rotated with respect to cup housing 6 in a clockwise direction to cause threaded driver 30 to be driven over cup housing 6, thus forcing mixing container 14 into supplemental container 28, as will be discussed below with reference to FIGS. 3A and 3B.

Figure 2:
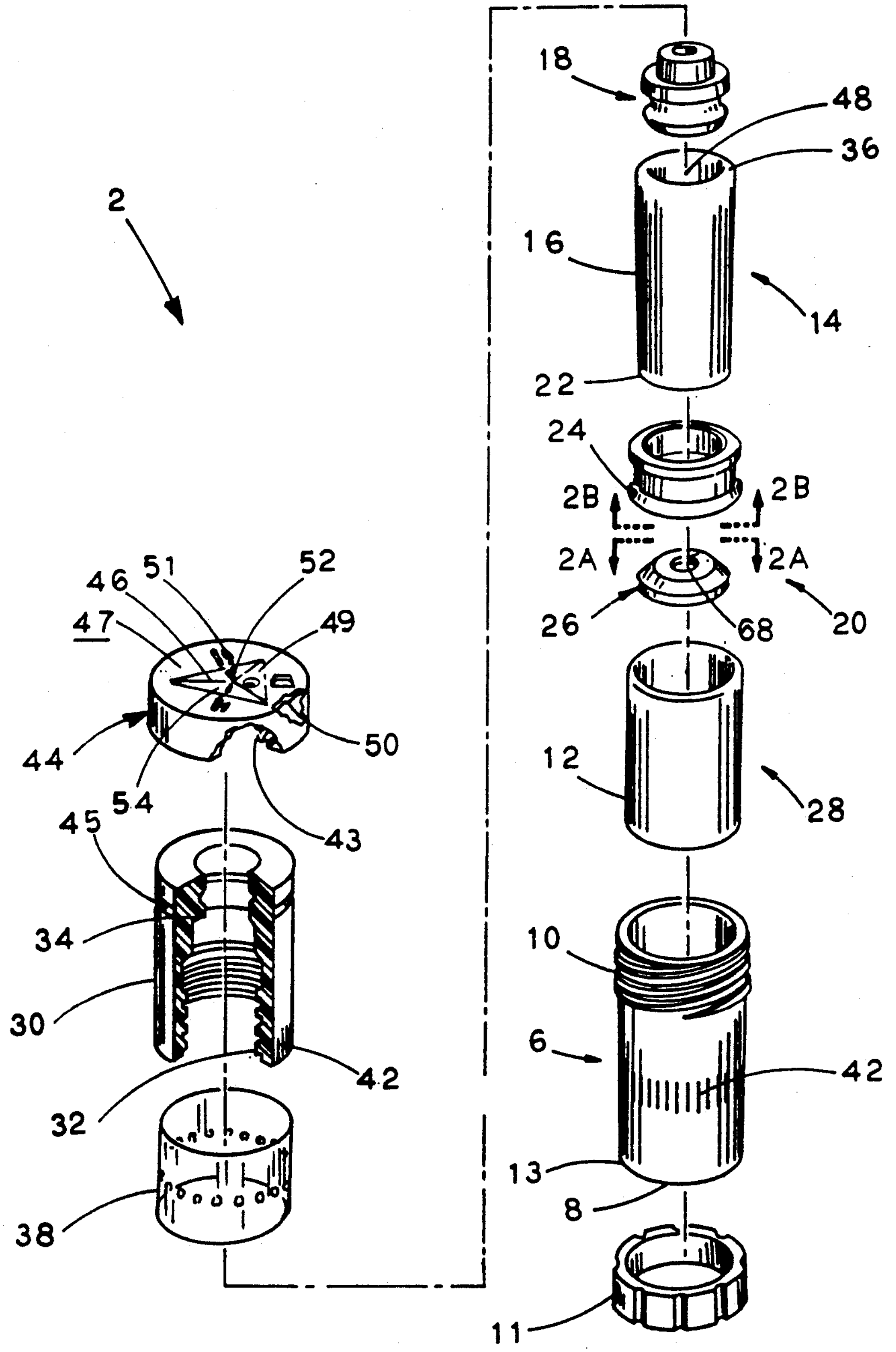
FIG. 2 is an exploded cross-sectional view of the mixing vial of FIG. 1.

Mixing vial 2 also includes a hard plastic, cap-shaped safety shield 44 having an internal annular bead 43 which engages an external circular groove 45 formed on the outside of threaded driver 30 generally opposite shoulder 34. Shield 44 prevents unauthorized access to the interior 48 of cylinder 16 by the use of a penetrating needle cannula prior to mixing of the components. Shield 44 has three thicker or deeper weakened regions 46 formed into its outer surface 47 and three thinner or shallower regions 49 formed into its inner surface 50; see FIGS. 2 and 3A. Shield 44 also has three pairs of mating catch elements 51, 52. Weakened regions 46 act as frangible, tamper-evident seams, while weakened regions 49 act as integral hinges which permit the triangular sections 54 to pivot from their normal, sealed positions of FIGS. 2 and 3A to their opened, in-use positions of FIGS. 3B and 3C, as is discussed below.

Figures 3A, 3B, 3C:
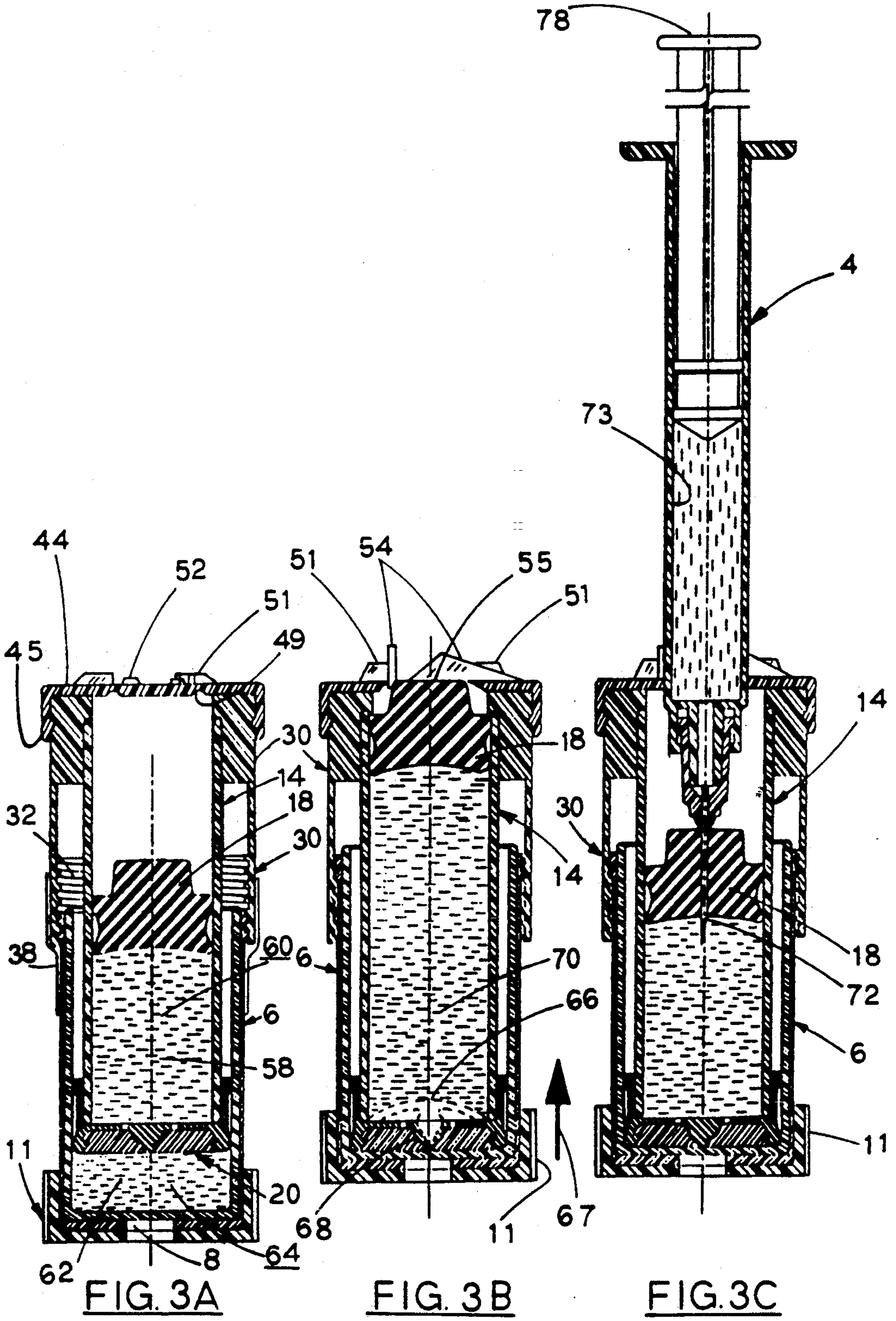
FIG. 3A is a cross-sectional view of the mixing vial of FIG. 1 in a pre-mixed condition.
FIG. 3B illustrates the mixing vial of FIG. 3A after the mixing and supplemental containers have been collapsed, placing the mixing vial in a post-mixed condition by screwing the two containers together, thereby mixing the pharmaceuticals in a relatively slow, controlled manner.
FIG. 3C shows the mixing vial of FIG. 3B in a post-aspiration condition with the needle cannula of a syringe passing through the piston and the syringe having withdrawn the mixed pharmaceutical from the mixing container into the syringe via the partial vacuum created within the syringe barrel, the piston moving to adjust the mixing chamber volume to match the withdrawn mixed pharmaceutical, the piston being driven by atmospheric pressure.
Figure 2A:
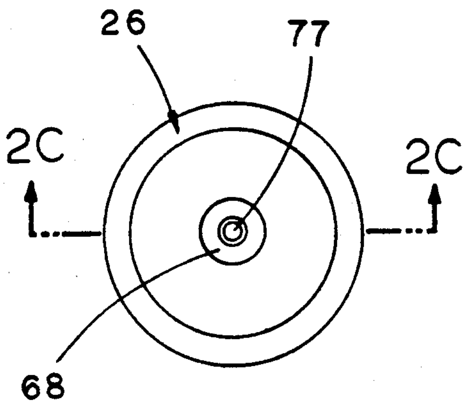
FIGS. 2A and 2B are views of the plastic insert and elastomeric seal of FIG. 2 taken along lines 2A—2A and 2B—2B, respectively.
Figure 2B:
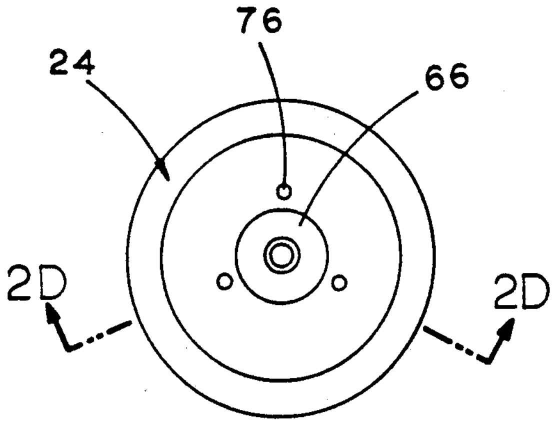
Figure 2C:
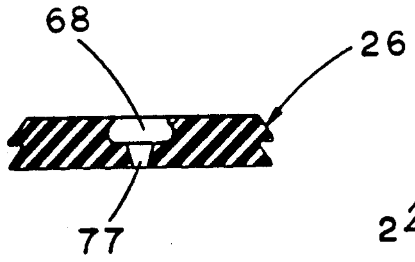
FIGS. 2C and 2D are cross-sectional views taken along lines 2C—2C and 2D—2D of FIGS. 2A and 2B, respectively.
Figure 2D:
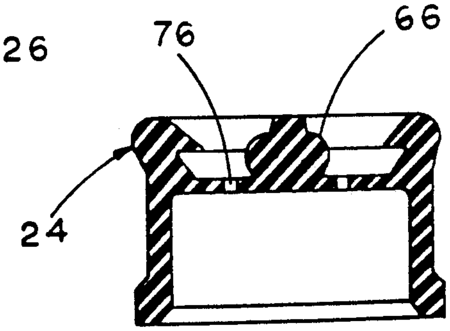

FIG. 3A illustrates mixing vial 2 in its pre-mixed condition with a first pharmaceutical 58 housed within a first variable volume region 60 defined within the interior 48 of glass cylinder 16 between barrier seal 20 and elastomeric piston 18. A second pharmaceutical 62 is housed within a second variable volume region 64 defined within glass cup 12 and bounded by barrier seal 20. End 45 of plug 44 is positioned in groove 46.

In FIG. 3A first and second pharmaceuticals 58, 62 are shown as liquid pharmaceuticals. However, first variable volume region 60 could contain lyopholized pharmaceutical crystals or the like.

FIG. 3B illustrates mixing vial 2 in its post-mixed condition with tamper-evident seal 38 removed after threaded driver 30 has been threaded onto cup housing 6 forcing barrier seal 20 farther into glass cup 12. Doing so causes the center portion 66 of elastomeric seal 24 to move in the direction of arrow 67 to a dashed-line position in FIG. 3B and become disengaged from within a hollow portion 68 of plastic insert 26. This permits fluid flow from second variable volume region 64, through a hole 77 and hollow portion 68 in insert 26, and through openings 76 formed in elastomeric seal 24 surrounding center portion 66. The movement of piston 18 from the position of FIG. 3A to the position of FIG. 3B causes the end 55 of piston 18 to press against inner surface 50 causing frangible weakened regions 46 to break permitting sections 54 to pivot from their positions of FIG. 3A to their positions of FIG. 3B. In FIG. 3B, sections 54 are secured in place by the frictional engagement of catch elements 52 with catch element 51. Other types of rupturable barriers, other than barrier seal 20, and other types of safety seals, other than safety shield 44, could be used as well.

To access the mixed pharmaceutical 70, the needle cannula 72 of syringe 4 is inserted through elastomeric piston 18 as shown in FIG. 3C. Mixed pharmaceutical 70 is forced from first variable volume region 60 into the interior 73 of syringe 4 by pulling on stem 78 of syringe 4. This creates a partial vacuum within the syringe to pull mixed pharmaceutical 70 from region 60, through needle cannula 72 and into syringe 4. Piston 18 moves a distance directly proportional to the volume of mixed pharmaceutical 70 aspirated, that is from the post-mixed condition of FIG. 3B to the post-aspiration condition of FIG. 3C.

In some situations it may not be desireable to access mixed pharmaceutical 70 using syringe 4. In such cases, piston 18 need not be pierceable by a needle cannula. Rather, piston 18 could be removable or it could include some other type of access member, such as a threaded plug, a capillary nick, a topical roller or a spray head.

Other modifications and variations can be made to the disclosed embodiment without departing from the subject of the invention as defined in the following claims. For example, although it is preferred that most of the components of mixing vial 2 be made of transparent materials, opaque or translucent materials could be used as well. The use of a threaded drive for collapsing supplemental container 28 and mixing container 14 can be replaced by other types of controlled drives, such as ratchet drives, if desired.

What is claimed is:

1. A controlled action mixing vial, for use with first and second pharmaceutical components, the second component being a liquid component, comprising:

a mixing container having first and second ends with openings at the first and second ends;

a piston positioned within the mixing container and movable from a pre-mix position, towards the second end, to a post-mix position, towards the first end;

a seal at the opening at the second end of the mixing container, the first component being within a first variable volume mixing region between the seal and the piston;

a supplemental container, containing the second component;

the mixing and supplemental containers being coaxially translating containers with the second end of the mixing container sealably positioned within the supplemental container, the second component being within a second variable volume region defined by the seal at the second end of the mixing container and supplemental container;

means for axially driving the mixing container into the supplemental container in a controlled manner to force the second component past the seal into the variable volume mixing region causing the first and second components to mix and forcing the piston towards the first end to the post-mix position; and the piston including means for permitting access to the mixture of the pharmaceutical components.

2. The vial of claim 1 wherein the axially driving means is a rotary drive by which first and second rotary drive elements associated with the supplemental and mixing containers, respectively, are rotated relative to one another.

3. The vial of claim 1, wherein the axially driving means rotates the mixing and supplemental containers relative to one another.

4. The vial of claim 1 wherein the piston is pierceable by a hollow needle at the post-mix position to permit the mixed contents within the variable volume region to be withdrawn through the hollow needle.

5. The vial of claim 1, wherein the seal includes a diaphragm with a pressure sensitive weakened region.

6. The vial of claim 1, wherein the mixing container is cylindrical and the supplemental container is cup shaped.

7. The vial of claim 1, further comprising a safety member displaceably mounted at the first end of the mixing container, said safety member being displaceable by said piston when said piston is in the post-mixed position.

8. The vial of claim 1, further comprising safety seal means for preventing access to the piston when the piston is at the pre-mix position.

9. The vial of claim 1, further comprising a tamper-evident element mounted to the mixing and supplemental containers when the piston is in the pre-mix position.

10. The vial of claim 1, further comprising means for indicating when the mixing container has been axially driven into the supplemental container.

11. A controlled action mixing vial, for use with first and second pharmaceutical components, the second component being a liquid component, comprising:

a mixing container having first and second ends with openings at the first and second ends;

a piston positioned within the mixing container and movable from a pre-mix position, towards the second end, to a post-mix position, towards the first end;

a seal at the opening at the second end of the mixing container, the first component being within a first variable volume mixing region between the seal and the piston;

a supplemental container, containing the second component;

the mixing and supplemental containers being coaxially translating containers with the second end of the mixing container sealably positioned within the supplemental container, the second component being within a second variable volume region defined by the seal at the second end of the mixing container and supplemental container;

means for axially driving the mixing container into the supplemental container in a controlled manner to force the second component past the seal into the variable volume mixing region causing the first and second components to mix and forcing the piston towards the first end to the post-mix position;

a safety member displaceably mounted at the first end of the mixing container, the safety member preventing access to the piston when the piston is at the pre-mix position, the safety member being displaceable by the piston when the piston is at the post-mix position; and the piston being piercable by a hollow needle at the post-mix position to permit the mixed contents within the variable volume region to be withdrawn through the hollow needle after the safety member has been displaced by the piston.

* * * * *